United States Patent

Bertram

[11] Patent Number: 5,819,733
[45] Date of Patent: Oct. 13, 1998

[54] TRANSPHARYNGEAL TUBE WITH PHARYNGEAL AND ESOPHAGEAL CUFFS, AND PROTECTED TIP

[75] Inventor: Volker Bertram, Sulz, Germany

[73] Assignee: VBM Medizintechnik GmbH, Sulz, Germany

[21] Appl. No.: 745,947

[22] Filed: Nov. 8, 1996

[51] Int. Cl.$^6$ .......................... A61M 16/00; A61M 29/00
[52] U.S. Cl. ............................ 128/207.15; 128/207.14; 128/911; 604/96; 604/101; 604/102
[58] Field of Search ........... 128/200.26, 207.14–207.17, 128/911, 912, DIG. 26; 604/96, 101, 102

[56] References Cited

U.S. PATENT DOCUMENTS

| | | | |
|---|---|---|---|
| 1,567,500 | 12/1925 | Hein | 128/207.15 |
| 2,099,127 | 11/1937 | Leech | 128/207.15 |
| 3,363,629 | 1/1968 | Kuhn | 128/207.15 |
| 3,616,799 | 11/1971 | Sparks | 128/207.15 |
| 3,659,612 | 5/1972 | Shiley et al. | 128/207.15 |
| 3,799,173 | 3/1974 | Kamen | 128/207.15 |
| 3,810,474 | 5/1974 | Cross | 128/207.15 |
| 3,989,571 | 11/1976 | Harautoneian | 128/207.15 |
| 4,230,108 | 10/1980 | Young . | |
| 4,231,365 | 11/1980 | Scarberry . | |
| 4,627,433 | 12/1986 | Lieberman . | |
| 4,976,261 | 12/1990 | Gluck et al. | 128/207.14 |
| 4,979,505 | 12/1990 | Cox | 128/207.15 |
| 5,309,906 | 5/1994 | LaBombard | 128/207.14 |
| 5,499,625 | 3/1996 | Frass et al. | 128/207.14 |
| 5,632,271 | 5/1997 | Brain | 604/96 |
| 5,642,730 | 7/1997 | Baran | 128/207.14 |

FOREIGN PATENT DOCUMENTS

| | | |
|---|---|---|
| 0596517 | 5/1994 | European Pat. Off. . |
| 3542260 | 6/1986 | Germany . |

*Primary Examiner*—Kimberly L. Asher
*Attorney, Agent, or Firm*—Paul J. Vincent

[57] ABSTRACT

A transpharyngeal tube (10), especially for intubation anaesthesia, has a tube shaft (13) on which an inflatable primary cuff (18) for blocking the pharynx (19) and an inflatable secondary cuff (16) for blocking the esophagus (12) are disposed. At least one application channel (20) is formed on or in the tube shaft (13) which has an application opening (21), located below the primary cuff (18), for application of substances into the trachea (14). The secondary cuff (16) surrounds a tube tip (11) of the tube shaft (13) which seats in the entrance region of the esophagus (12) on an inner wall (15) thereof when the transpharyngeal tube (10) is inserted. This configuration of the transpharyngeal tube (10) facilitates a safe, reproduceable, and directed insertion into the esophagus (12) with which a safe and painless securing of the transpharyngeal tube (10) and controlled application of the application substance into the trachea (14) are guaranteed.

11 Claims, 2 Drawing Sheets

Fig. 2
Fig. 3
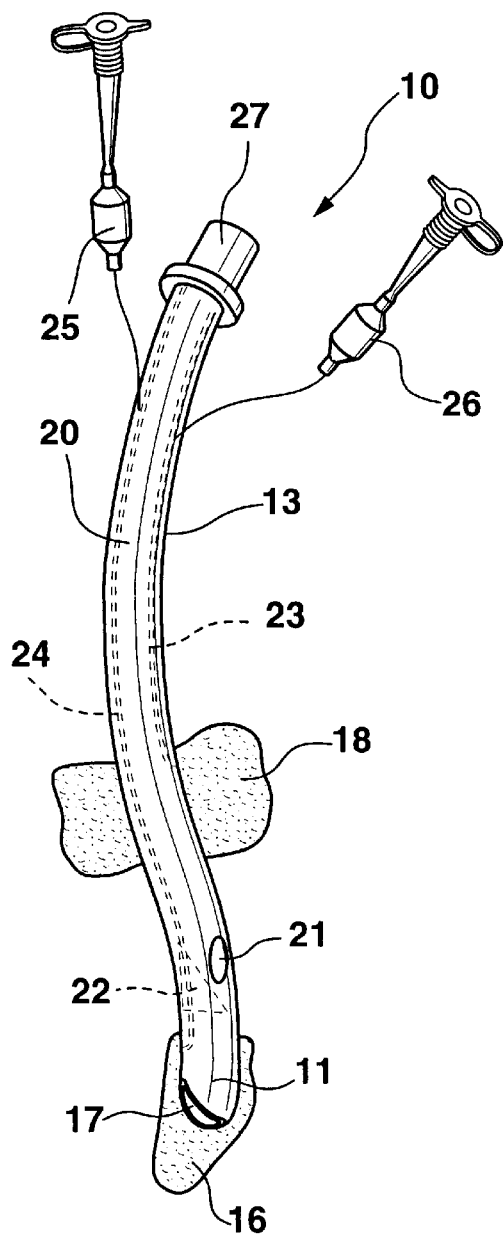
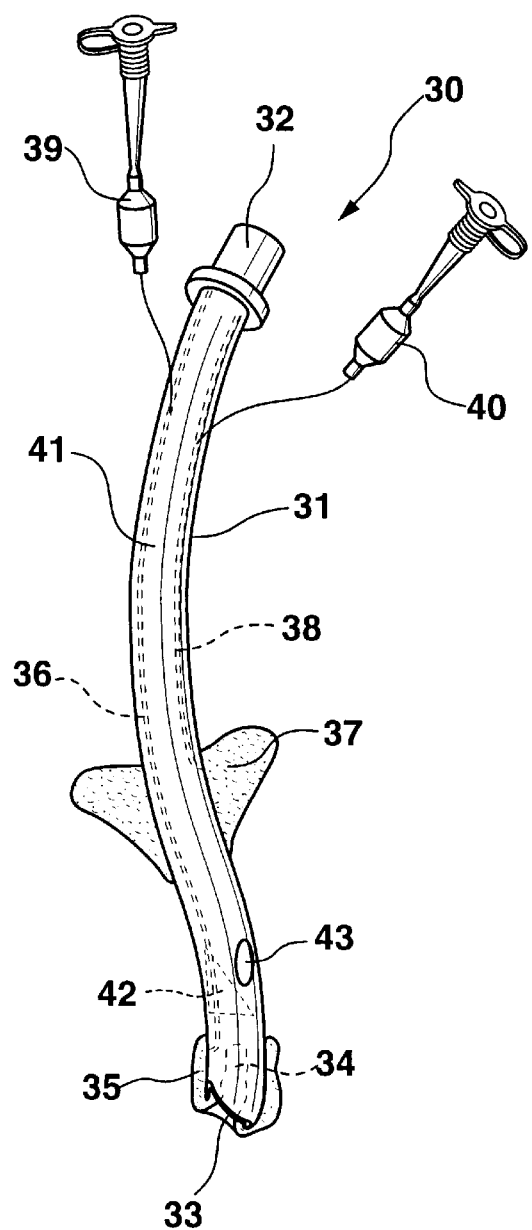

TRANSPHARYNGEAL TUBE WITH PHARYNGEAL AND ESOPHAGEAL CUFFS, AND PROTECTED TIP

BACKGROUND OF THE INVENTION

The present invention concerns a transpharyngeal tube, especially for intubation anaesthesia, having a tube shaft on which an inflatable primary cuff for blocking the pharynx and an inflatable secondary cuff for blocking the esophagus are disposed and in or on which at least one application channel is formed having an application opening below the primary cuff for application of substances into the trachea.

A tube of this kind having two cuffs and an application opening disposed between the cuffs has become known in the art through U.S. Pat. No. 4,230,108.

In one possible application of intubation anaesthesia, an esophageal tube is introduced into the esophagus normally after administering premedication, following previously induced initial intravenous anaesthesia, or subsequent to inhaled anaesthesia using an anaesthesia mask. The esophageal tube comprises one or a plurality of inflatable cuffs for a gas and liquid-tight sealing of the space located between the trachea and a tube shaft of the esophageal tube.

The trachea is sealed off after insertion of the esophageal tube through blocking by the cuffs in the esophagus and in the pharynx so that an open breathing passage for the patient which is separate from the esophagus is continuously accessible via the tube application channel and, in particular, no mixing between vomitted stomach contents and respiratory air can occur.

The esophageal tube application channel henceforth facilitates artificial respiration of the patient and, if appropriate, anaesthetic can be inhaled when an anaesthetic substance, for example an air-anaesthetic or $O_2$-anaesthetic mixture, is introduced.

Intubation anaesthesia is utilized with patients who must be anaesthetized for a longer period of time or when aspiration is endangered due to a full stomach.

The esophageal tube known in the art from U.S. Pat. No. 4,230,108 is introduced into the esophagus and subsequently blocked in the pharynx via a primary cuff and in the esophagus via a secondary cuff. An application channel is formed at a tube wall of the conventional tube which has openings in the outer tube wall in the form of perforations facing the entrance to the trachea. Medication can be introduced into the trachea at the trachea entrance via these perforations.

This esophageal tube is inserted deep into the esophagus and causes irritation of a greater or lesser extent which can lead to undesirable reactions such as reduced stress response in the form of circulatory system reaction. This irritation is compensated for either by means of a local anaesthetic, by coating the tube with a gel containing a local anaesthetic or by increasing the anaesthetics. When the effects of local anaesthetics have worn off, the irritation caused by the tube must be compensated for by increased anaesthesia.

When patients are anaesthetized, natural reflexes such as coughing and the like are either not present or are at least weakened due to the general central weakening of reflexes or to muscle relaxation so that respiration is endangered.

Instead of initiating intubation anaesthesia, it is also possible to e.g. institute inhalation anaesthesia with the use of a larynx mask. Towards this end, the anaesthetic, e.g. an air-anaesthetic or $O_2$-anaesthetic mixture, is administered to the patient by introduction of a specially shaped mask into the larynx which can provide similar sealing behaviour as the above-mentioned tube.

However, larynx mask inhalation anaesthesia has limited use. For example, it cannot be used for patients requiring anaesthesia who have full stomachs. Moreover, aspiration is endangered if the larynx mask is improperly positioned.

Other operative or therapeutic methods utilize an endotracheal tube for respiration or anaesthesia which is introduced into the trachea either nasally or orally. With such a tube the tube tip and a cuff of the endotracheal tube must be inserted through the vocal cords into the trachea to block-off the trachea. This intubation method can be carried out only with the additional use of a laryngoscope. As a result, this type of intubation procedure can have disadvantageous complications for the patient.

The esophageal tube known in the art through U.S. Pat. No. 4,230,108 facilitates respiration of or anaesthetizing the patient using an inserted tube which does not require intubation through the vocal cords and which eliminates aspiration of stomach contents with the assistance of a blocking secondary cuff. In order to facilitate these functional features it is necessary for the conventional tube to be introduced relatively deeply into the esophagus. This has the above-mentioned disadvantage of painful distress to the patient.

Since it is necessary to introduce the tube into the esophagus rapidly and without loss of time, the conventional tube may not be inserted into the esophagus but rather incorrectly introduced into the trachea. A directed introduction into the esophagus is difficult and must, if necessary, be attempted and repeated a plurality of times. This leads to an unnecessary loss of time during operative treatment of the patient, to auxiliary application of anaesthesia, to additional painful patient distress and finally to a possible interruption of the intubation.

It is therefore the underlying purpose of the invention to further improve the conventional tube in such a fashion that a reliable reproducible and irritation-free blocking of the esophagus is facilitated which guarantees a secure seating and fixing of the tube in as painless a fashion as possible and controlled application of the application substance into the trachea.

SUMMARY OF THE INVENTION

This purpose is achieved in that the tube shaft has an S-shaped longitudinal profile and the secondary cuff completely surrounds a tube tip of the tube shaft ending in the entrance region of the esophagus when the transpharyngeal tube is inserted.

Since the tube tip is only inserted into the entrance region of the esophagus with the secondary cuff only blocking this entrance region, a painful stressing of the esophagus is avoided on behalf of the patient. The secondary cuff surrounds the tip of the tube in the activated state to prevent constant contact of the tube tip which could cause excessive stress to the inner wall in the entrance region of the esophagus. The entrance port to the esophagus is occluded in a gas- and liquid-tight fashion when the secondary cuff is activated.

If the secondary cuff is filled to an inner pressure of at least 50 cm of $H_2O$ and the inner pressure of the primary cuff is approximately 80 to 100 cm of $H_2O$, both cuffs are in good contact with the mucous membranes of the esophagus entrance and the pharynx. The internal pressure of both cuffs can subsequently be reduced to approximately 20 cm of $H_2O$ with the tube shaft being properly seated to guarantee optimum sealing.

When the responsible physician introduces the transpharyngeal tube in accordance with the invention beyond the pharynx into the body of a patient, the tube tip is positioned into the entrance region of the esophagus in a safe and self-orienting fashion by the S-shaped bending of the tube shaft. The transpharyngeal tube in accordance with the invention guarantees that the tube tip is automatically properly positioned in the esophagus entrance region and intubation can be carried out in a rapid and controlled fashion. The secondary cuff is subsequently inflated so that the tube tip cannot further penetrate or be inserted into the esophagus to cause painful stress thereto. The primary cuff is subsequently blocked so that the trachea is only accessible via the application channel. Respiration as well as introduction of anaesthesia are effected via the application channel. It is also possible to insert a suction catheter into the trachea via the application channel. The suction catheter slides in a directed fashion through the lumen of the transpharyngeal tube and is safely guided into the trachea by the shape of the blocking element.

A proper coordinated disposal of the primary cuff, the secondary cuff, and the application opening on an S-shaped tube shaft facilitates proper placement of the transpharyngeal tube in the entrance region to the esophagus so that the application opening is always located at the entrance to the trachea.

Particularly preferred embodiments of the invention are given in the dependent claims.

In a preferred embodiment, the tube tip has a seating surface adapted to a contour of the esophagus for seating on the inner wall in the entrance region of the esophagus. In this manner the tube tip of the esophageal tube in accordance with the invention can seat on or adapt to the inner wall of the entrance region of the esophagus in a particularly advantageous fashion. The S-shaped tube shaft is somewhat resilient so that the tube tip is pressed onto the inner wall. For this reason the tube tip can be easily fixed in the entrance region of the esophagus and the internal pressure of the secondary cuff is reduced. In consequence thereof the tube tip can seat in the entrance region of the esophagus in a manner which is more gentle to the patient.

In another likewise preferred embodiment, a cavity is formed in the vicinity of the tube tip for the acceptance of a portion of the inflatable secondary cuff in the non-activated state thereof. Prior to introduction of the transpharyngeal tube, the inflatable secondary cuff is folded together and introduced into the cavity of the tube tip. The secondary cuff can be attached to an outer wall of the tube shaft so that a portion of the secondary cuff can be pushed into the cavity in its folded-together state. It would, however, also be conceivable to secure the secondary cuff inside the cavity so that the secondary cuff can be accommodated within the cavity in its entirety when folded together. Accommodation of the secondary cuff within the cavity has the advantage that insertion of the transpharyngeal tube is simplified since the tube tip can be thin and can be adapted to the diameter of the tube shaft. The secondary cuff in the tip region does not lead to any substantial widening of the tip.

The cavity is particularly easy to realize when it is formed by a portion of the open application channel which is separated from an upper portion of the application channel by means of a blocking element placed into the application channel. An open application channel can therefore be formed during manufacture of the transpharyngeal tube which can be retroactively subdivided using the blocking element. The blocking element can have differing shapes and can e.g. be formed by a membrane. The blocking element serves to securely and permanently interrupt the lumen, which is utilized as an application channel, in the direction towards the tube tip. The cavity in the tube tip is always separated from the application channel.

It is preferred when the blocking element constitutes a means for facilitating flow of applied substances towards the application opening. The blocking element can either have an appropriate shape or can be disposed in the application channel in such a fashion that application substance flowing through the application channel, for example a local anaesthetic, is guided directly towards the application opening. An application substance flowing with low pressure through the application channel can thereby also be easily introduced through the application opening into the trachea. Conversely, the means for facilitating flow can direct respiratory air into the application channel and also exhaust therethrough.

In the event that the application opening is formed by a plurality of openings, the application substance which is flowing-in can be finely distributed in the trachea. The application opening is preferentially slot-shaped towards the epiglottis and widens in a drop-shaped fashion towards the secondary cuff.

In an additional embodiment the primary and/or the secondary cuff are configured as low-pressure cuffs. This has the advantage that the tissue surfaces of the pharynx or of the esophagus on which the cuffs seat are gently treated.

It is also preferred when channels are provided for in the tube wall for inflation of the primary and of the secondary cuffs. In this fashion both cuffs can be utilized independently of each other for blockage of body cavities. Each cuff is connected to its own inlet channel so that each cuff can be separately inflated and individually adjusted to the patient.

In the event that the primary and secondary cuffs are fashioned in such a manner that they are resistant to permeation, it is not possible for anaesthetic gas to diffuse into the cuff to cause an undesired change in the inner pressure of the cuff.

In additional embodiments, the primary cuff is either cylindrical, pear-shaped and/or has a corrugated outer surface. The shape of the primary cuff allows for optimation of the seating properties on the inner wall of the pharynx, of the blocking properties, and of the securing of the tube shaft. The different shapes of the primary cuff which include, in addition to the preferred forms and surface configurations, other shapes adapted to the contours of the body cavities, facilitate adjustment of the outer contour of the primary cuff to differently shaped regions of the pharynx of different patients.

The tube shaft is manufactured from an elastic plastic to guarantee that the tube shaft can be introduced in a controlled manner. A tube shaft made from this type of material can have a stable S-shaped longitudinal profile while simultaneously permitting small shape changes to facilitate gentle introduction into the esophagus of the patient. In addition the elastic material facilitates a slightly resilient and pressurized seating of the tube tip on the inner wall of the entrance region of the esophagus.

The transpharyngeal tube in accordance with the invention can be configured as a disposable instrument or as a tube which can be sterilized a plurality of times.

Further advantages can be derived from the description of the accompanying drawings of an embodiment of the invention. The above-mentioned features of the claims can be utilized in accordance with the invention individually or collectively in arbitrary combination. The embodiments mentioned are not to be considered as exhaustive enumeration rather have exemplary character. The invention is represented in the drawing and is described more closely with reference to the embodiments.

BRIEF DESCRIPTION OF THE DRAWING

FIG. 2 shows the transpharyngeal tube according to FIG. 1 having a cylindrical primary cuff and an inflated secondary cuff;

FIG. 3 shows an additional transpharyngeal tube in accordance with the invention having a pear-shaped primary cuff and a secondary cuff which is partially inserted into a cavity of the tube tip.

DESCRIPTION OF THE PREFERRED EMBODIMENT

Figure 1:
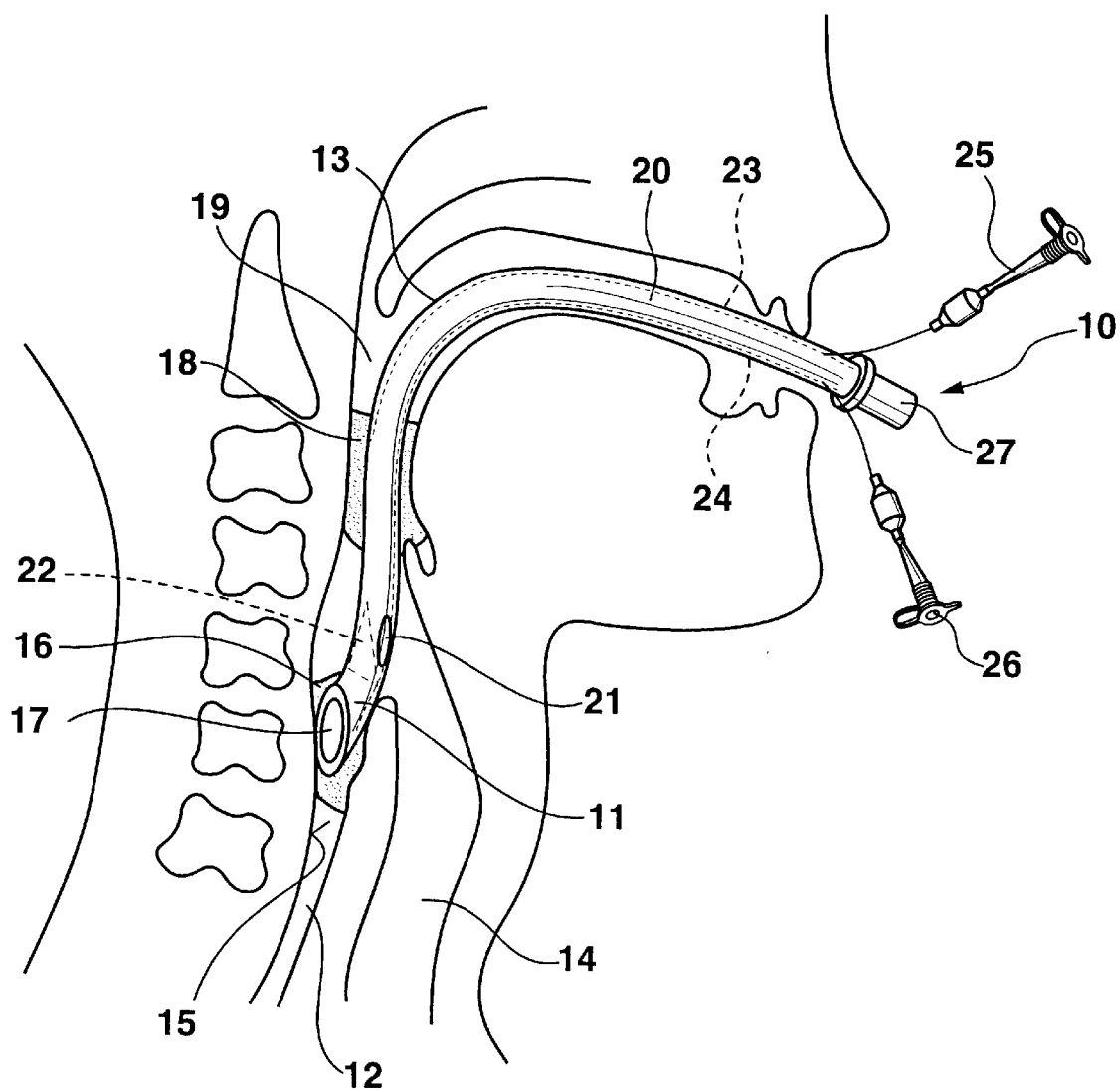
FIG. 1 shows a schematic cut through the entrance region of the esophagus into which a transpharyngeal tube in accordance with the invention is introduced.

The individual figures of the drawing partially show the object in accordance with the invention in a highly schematic fashion and are not to be taken to scale. The objects of the individual figures are partially strongly reduced or enlarged so that their construction can more easily be illustrated.

FIG. 1 shows a transpharyngeal tube 10, the tube tip 11 of which is inserted into the entrance region of the esophagus 12. The transpharyngeal tube 10 comprises a tube shaft 13 having an S-shaped longitudinal profile. The S-shaped longitudinal profile guarantees that the transpharyngeal tube 10 is always introduced into the entrance region of the esophagus 12 and not incorrectly into the trachea 14. The S-shaped formation of the tube shaft 13 made from a flexible elastic plastic causes the tip of the tube 11 to seat in a lightly pressurized fashion on the inner wall 15 of the esophagus due to the resilient action of the tube shaft 13. The tube tip 11 is thereby fixed at the entrance region of the esophagus 12. A secondary cuff 16 is inflated for fixing the tube tip 11 in this position to block the entrance region of the esophagus 12 in a gas- and liquid-tight fashion. The secondary cuff 16 is folded together when introducing the transpharyngeal tube 10 and inserted into cavity 17 of the tube tip 11 so that the transpharyngeal tube 10 can be easily inserted. The secondary cuff can also be disposed at the tube tip 11 in such a fashion it does not increase the outer diameter of the tube tip 11.

The pharynx 19 is blocked by an inflatable primary cuff 18. Blockage of the primary cuff 18 and the secondary cuff 16 likewise causes blockage of the trachea 14 which is only accessible via application channel 20. Via the application channel 20, the patient being treated is both respirized as well as anaesthetized with additional application substances. Application substances can flow through the application channel 20 and application opening 21 into the trachea. The application channel 20 is formed as a passage through the tube shaft 13 and is subdivided by means of a blocking element 22 into an upper portion used for applications and the hollow cavity 17 of the tube tip 11. The blocking element 22 constitutes a means for facilitating flow to deflect an inwardly flowing application substance onto the application opening 21. The application opening 21 can have widely differing shapes. Circular, oval, slot shaped and drop-shaped combinations of the previously mentioned shapes are preferred for the application opening.

The primary cuff 18 and the secondary cuff 16 can be inflated by means of channels 23 and 24 which are separately formed in the tube shaft 13 and travel in the tube shaft 13 wall. The channels 23 and 24 are each connected to checking devices 25 and 26 so that the primary cuff 18 and the secondary cuff 16 can be inflated in a regulated fashion to an adjustable internal pressure. A connecting means 27 (e.g. a Luer-locking connection) facilitates connection of the transpharyngeal tube 10 to conventional intubation devices known in the art.

FIG. 2 shows the transpharyngeal tube 10 in accordance with the invention. The transpharyngeal tube 10 comprises, at one end, the connecting means 27 for connection of the transpharyngeal tube 10 to intubation devices and the tube tip 11 at the other end. The tube tip 11 is surrounded by a secondary cuff 16 which can be folded together in the non-inflated state and inserted into the cavity 17 so that the transpharyngeal tube can be inserted gently. The primary cuff 18 is cylindrically shaped so that large portions of the outer contour of the primary cuff 18 can seat on portions of the pharynx.

Channels 23 and 24 are formed in a tube shaft 13 wall and guarantee separate activation of the primary cuff 18 and the secondary cuff 16. The channels 23 and 24 are connected to the checking devices 25 and 26 for inflation of the primary cuff 18 and the secondary cuff 16 to an adjustable internal pressure. The application channel 20 is formed in the tube shaft 13 and extends from the connecting means 27 up to the tube tip 11. The application channel 20 is permanently subdivided in a gas- and liquid-tight fashion by a blocking element 22 into an upper part for applications and a lower cavity 17 into which the secondary cuff 16 can be inserted in a folded together state for introduction of the transpharyngeal tube 10. An application substance, e.g. an anaesthetic, can flow into the trachea via the application opening 21.

FIG. 3 shows a transpharyngeal tube 30 in a state prior to introduction into the esophagus of the patient. A connecting means 32 is formed on one end of the tube shaft 31 for connection to conventional intubation devices and a tube tip 33 is formed on the other end. The tube tip 33 has a cavity 34 into which a part of the secondary cuff 35 is inserted. The transpharyngeal tube 30 can therefore be easily inserted into the esophagus of the patient, since the secondary cuff 35 does not interfere with this insertion.

When the tip of the tube 33 seats in the entrance region of the esophagus, the secondary cuff 35 is activated and inflated via a channel 36 formed in a wall of the tube shaft 31.

An inflatable primary cuff 37 is pear-shaped to guarantee that the primary cuff 37 can only be inserted up to a particular location in the pharynx. This also guarantees that the esophageal tube 30 is not inserted past the entrance region of the esophagus into the esophagus. The primary cuff 37 is likewise inflatable by means of a channel 38 formed in the wall of the tube shaft 31. The channels 36 and 38 are connected to checking devices 39 and 40 which facilitate controlled activation of the primary cuff 37 and of the secondary cuff 35 to adjust internal pressure.

The tube shaft 31 has an application channel 41 which forms a passage through the tube shaft 31. A blocking element 42 subdivides the application channel 41 into a portion for application of an application substance into the trachea via an application opening 43 and into the cavity 34.

The embodiments of the transpharyngeal tubes in accordance with the invention shown in the figures are manufactured from plastic and can have differing softnesses and temperature stabilities.

A transpharyngeal tube 10, especially for intubation anaesthesia, has a tube shaft 13 on which an inflatable primary cuff 18 for blocking the pharynx 19 and an inflatable secondary cuff 16 for blocking the esophagus 12 are disposed. At least one application channel 20 is formed on or in the tube shaft 13 which has an application opening 21, located below the primary cuff 18, for application of substances into the trachea 14. The secondary cuff 16 surrounds a tube tip 11 of the tube shaft 13 which seats in the entrance region of the esophagus 12 on an inner wall 15 thereof when the transpharyngeal tube 10 is inserted. This configuration of the transpharyngeal tube 10 facilitates a safe, reproduceable, and directed insertion into the esophagus 12 with which a safe and painless securing of the transpharyngeal tube 10 and controlled application of the application substance into the trachea 14 are guaranteed.

I claim:

1. A transpharyngeal tube for introducing substances into a trachea, for intubation anaesthesia and for blocking a pharynx and an esophagus the tube comprising:

an inflatable primary cuff for blocking the pharynx;

a tube shaft on which said inflatable primary cuff is disposed, said shaft having a S-shaped longitudinal profile and a tube tip ending at an entrance region of the esophagus when the transpharyngeal tube is inserted, said tube shaft also having an application channel with an application opening located below said inflatable primary cuff for introducing substances into the trachea; and an inflatable secondary cuff disposed on said tube shaft for blocking the esophagus, said secondary cuff completely surrounding said tube tip.

2. The transpharyngeal tube of claim 1, wherein said tube tip has a contoured surface for seating on an entrance region of the esophagus.

3. The transpharyngeal tube of claim 1, wherein said tube shaft has a cavity in a vicinity of said tube tip for holding a portion of said inflatable secondary cuff in a non-inflated state thereof.

4. The transpharyngeal tube of claim 3, further comprising a blocking element disposed in said application channel to subdivide said application channel into an upper part and a lower part, said cavity being formed by said lower part.

5. The transpharyngeal tube of claim 4, wherein said blocking element facilitates flow of applied substances towards said application opening.

6. The transpharyngeal tube of claim 1, wherein at least one of said primary cuff and said secondary cuff is a low-pressure cuff.

7. The transpharyngeal tube of claim 1, wherein said tube shaft comprises a tube wall having a channel for inflation of said primary cuff and a channel for inflation of said secondary cuff.

8. The transpharyngeal tube of claim 1, wherein said primary cuff and said secondary cuff are manufactured from a permeation-resistant material.

9. The transpharyngeal tube of claim 1, wherein said primary cuff is cylindrical.

10. The transpharyngeal tube of claim 1, wherein said primary cuff is pear-shaped.

11. The transpharyngeal tube of claim 1, wherein said tube shaft is manufactured from an elastic plastic.

* * * * *